United States Patent [19]

Hartenstein et al.

[11] 4,294,834
[45] Oct. 13, 1981

[54] AZOCINE ANALGESICS AND METHOD FOR THEIR PREPARATION

[75] Inventors: Johannes Hartenstein, Stegen-Wittental; Gerhard Satzinger, Denzlingen; Heinrich Bahrmann, Kirchzarten; Volker Ganser, Freiburg, all of Fed. Rep. of Germany

[73] Assignee: Godecke Aktiengesellschaft, Freiburg, Fed. Rep. of Germany

[21] Appl. No.: 93,314

[22] Filed: Nov. 13, 1979

[30] Foreign Application Priority Data

Nov. 15, 1978 [DE] Fed. Rep. of Germany ....... 2849472
Jul. 7, 1979 [DE] Fed. Rep. of Germany ....... 2927501

[51] Int. Cl.$^3$ ................. C07D 221/22; A61K 31/435
[52] U.S. Cl. .................................... 424/260; 546/45; 546/75
[58] Field of Search .................... 546/45, 74; 424/260

[56] References Cited

U.S. PATENT DOCUMENTS 3,217,006 11/1965 Sawa .................................. 260/285
3,919,237 11/1975 Halder ................................ 260/285
4,139,534 2/1979 Lim ..................................... 546/74

OTHER PUBLICATIONS

Fieser et al., "Reagents for Organic Synthesis" pp. 68–77.
Sugasawa et al., Chem. Ber. 73, 782 (1940).
Knabe et al., Chem. Ber. 99, 2873 (1966).
Prudnommeaux et al., Eur. J. Med. Chem. Chimther 10, p. 19 (1975).
Knabe et al., Archv. Pharm. 297, 9 (1964).

Primary Examiner—Mark L. Berch
Attorney, Agent, or Firm—Stephen I. Miller

[57] ABSTRACT

Novel azocine derivatives and a method for their preparation are disclosed. The compounds display analgesic effects in mammals.

22 Claims, No Drawings

AZOCINE ANALGESICS AND METHOD FOR THEIR PREPARATION

BACKGROUND OF THE INVENTION

The oxidative cyclization of 3-benzyl-1,2,3,4-tetrahydroisoquinolines has hitherto not been described in the literature. This reaction, which proceeds with a high degree of regioselectivity, could not have been predicted and is surprising. Thus, the present invention provides a new class of compounds.

SUMMARY OF THE INVENTION

The invention relates to a compound of the formula I

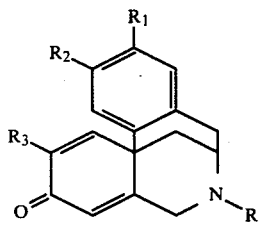

wherein R is hydrogen, straight or branched chain alkyl of from 1 to 8 carbon atoms, straight or branched chain alkenyl of from 2 to 6 carbon atoms, straight or branched chain alkynyl of from 2 to 6 carbon atoms, cycloalkyl containing 3 to 7 carbon atoms, cycloalkylalkyl containing 4 to 8 carbon atoms, 2- or 3-furylmethyl optionally substituted by 1 to 3 methyl groups, 2- or 3-tetrahydrofurylmethyl optionally substituted by 1 to 3 methyl groups or

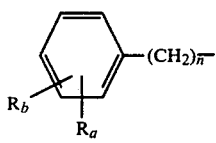

wherein n is an integer of 1 to 3, $R_a$ is hydrogen, monohalo, or dihalo, and $R_b$ is hydrogen hydroxy, methyl, trifluoromethyl, mono, di or trialkoxy of from 1 to 3 carbon atoms, alkanoyloxy of from 1 to 6 carbon atoms or $R_a$ and $R_b$ together form a methylenedioxy group; $R_1$ is hydroxy or alkoxy of from 1 to 6 carbon atoms; $R_2$ is hydrogen or alkoxy of from 1 to 6 carbon atoms; $R_1$ and $R_2$ when taken together may form a methylenedioxy group; $R_3$ is alkoxy of from 1 to 6 carbon atoms or benzyloxy; and the pharmacologically acceptable salts thereof.

The preferred compounds of formula I are those wherein R is hydrogen, branched or straight chain alkyl of from 1 to 3 carbon atoms, branched or straight chain alkenyl of 2 to 5 carbon atoms, cycloalkylalkyl of from 4 to 8 carbon atoms, or benzyl or phenethyl the aromatic rings of which may be optionally substituted by from 1 to 3 alkoxy groups of 1 to 3 carbon atoms or methylenedioxy; $R_1$ is hydroxy or alkoxy of from 1 to 3 carbon atoms; $R_2$ is hydrogen or alkoxy of from 1 to 3 carbon atoms; $R_1$ and $R_2$ when taken together may form a methylenedioxy group; $R_3$ is alkoxy of 1 to 3 carbon atoms; and the pharmacologically acceptable salts thereof.

The most preferred compounds of formula I are those wherein $R_1$ and $R_3$ may be the same or different and are methoxy or ethoxy, $R_2$ is hydrogen, methoxy or ethoxy, R is hydrogen, methyl, cyclopropylmethyl, branched or straight chain alkenyl of 2 to 5 carbon atoms, or 3,4-dimethoxyphenethyl, and the pharmacologically acceptable salts thereof.

The invention also relates to a method for preparing the compounds of formula I, and the pharmacologically acceptable salts thereof. This method comprises the oxidative cyclization of a compound of formula II

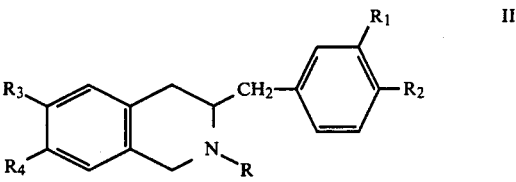

wherein R, $R_1$, $R_2$ and $R_3$ are as defined above and $R_4$ is hydroxy, alkoxy of from 1 to 6 carbon atoms or benzyloxy. The method also relates to the optional N-substitution of a product obtained upon oxidative cyclization of a compound of formula II wherein R is hydrogen. The method further relates to the preparation of the pharmacologically acceptable salts of the compounds of formula I.

The invention also relates to methods for using the compounds of formula I and their pharmacologically acceptable salts as analgesic agents for the treatment of mammals.

The invention also relates to pharmaceutical compositions comprising an analgesic effective amount of a compound of formula I and the pharmacologically acceptable salts thereof, as well as mixtures thereof.

DESCRIPTION OF THE INVENTION

The compounds of formula I are prepared by the oxidative cyclization of a compound of formula II. The starting materials of formula II are either known compounds or can be prepared by procedures described in the literature. See, for example, Arch. Pharm., 297, 129 (1964); Ber., 99, 2873 (1966); Ber., 73, 782 (1940); Eur. J. Med. Chem., 10, 19 (1975). According to the invention, a compound of formula II is added, with simultaneous cooling, to a solvent such as trifluoroacetic acid. A non-reactive co-solvent such as a haloalkane, e.g., methylene chloride, may also be used, when needed to increase the solubility of the reactants. The mixture is then treated with an oxidizing agent such as vanadyl trifluoride or vanadyl trichloride at a temperature of from about $-15°$ to about $+30°$ C. and preferably at a temperature of about $-15°$ to about $-5°$ C. The oxidizing agent is conveniently added during about 5 to about 15 minutes, this time is not critical and may vary, for example, depending on the quantity of oxidizing agent being added. During the reaction, the mixture temporarily assumes a dark blue to red-violet color. After completing the addition, the reaction mixture is stirred for an additional 0.5 to about 2 hours at a temperature of about $-10°$ to about $0°$ C. and the solvent is then evaporated in vacuum at a temperature maintained below about 20° C. The residue is then purified in a known manner. For example, it may be partitioned between water and an organic solvent such as chloroform methylene chloride dichloroethylene and the like; chloroform is preferred. The organic phase is treated with dilute base, for example, a 10–15% aqueous ammonia solution, dried and evaporated. Purification of this residue by recrystallization and/or chromatographic means provides the compounds of formula I as the free base. Alternatively, the residue from the evaporation of the reaction solvent may be treated with dilute base and extracted with an organic solvent such as chloroform. Further purification is carried out substantially as described above.

The oxidation is preferably carried out with the exclusion of moisture in an atmosphere of a non-reactive dry gas such as dry nitrogen.

It has been observed that the use of an excess of oxidizing agent will favor a quantitative reaction. Thus, near-quantitative yields are obtained when the molar ratio of oxidizing agent to starting material is about 2.5 to 1.

The oxidizing agents utilized are those which are preferably completely soluble in the reaction phase, and have a sufficient oxidation potential to carry out the desired molecular transformation. Vanadyl trifluoride is a particularly suitable oxidizing agent for use when the starting material does not contain phenolic groups, and vanadyl trichloride is particularly suitable when the starting material does contain phenolic groups.

Certain N-substituents, R, may inhibit the cyclization process due either to their steric bulk or to their sensitivity to the oxidizing reagent. It is within the skill of the art to recognize such substituents which are preferably added to the molecule after cyclization. In this alternative the cyclization is carried out using an N-unsubstituted starting material (i.e., compound II wherein R=H) thereby producing the N-unsubstituted product (compound I wherein R=H). The thus produced compound of formula I can then be N-substituted in known manner, for example, by reaction with a compound, R'—X wherein R' is straight or branched chain alkyl of from 1 to 8 carbon atoms, straight or branched chain alkenyl of from 2 to 6 carbon atoms, straight or branched chain alkynyl of from 2 to 6 carbon atoms, cycloalkyl containing 3 to 7 carbon atoms, cycloalkylalkyl containing 4 to 8 carbon atoms, 2- or 3-furylmethyl optionally substituted by 1 to 3 methyl groups, 2- or 3-tetrahydrofurylmethyl optionally substituted by 1 to 3 methyl groups or

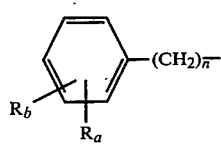

wherein n is an integer of 1 to 3, $R_a$ is hydrogen, monohalo, or dihalo, and $R_b$ is hydrogen hydroxy, methyl, trifluoromethyl, mono, di or trialkoxy of from 1 to 3 carbon atoms, alkanoyloxy of from 1 to 6 carbon atoms or $R_a$ and $R_b$ together form a methylenedioxy group. X is a substituent known to those skilled in the art as a "leaving group". Examples of such groups are halides and sulfur-containing groups such as p-toluenesulfonyloxy. The preferred groups, X, are the halides particularly chlorides and bromides. N-Substitution can also be achieved, by acylation followed by reduction of the amide function with, for example, lithium aluminum hydride. In this case the keto group of the cyclohexadienone ring must be either temporarily protected, for example, by ketal formation, or subsequently reformed by oxidation of diene alcohol produced after reduction.

The conversion of the free base forms of the compounds of the invention into their pharmacologically acceptable salts can be carried out by neutralization with an appropriate organic or inorganic acid, for example, hydrochloric acid, sulphuric acid, phosphoric acid, hydrobromic acid, acetic acid, fumaric acid, oxalic acid, lactic acid, citric acid, malic acid, salicylic acid, malonic acid, maleic acid, succinic acid, ascorbic acid, and the like. The salts are converted back to their respective free bases by treatment with a base such as dilute sodium or potassium hydroxide or dilute ammonia. The free amines and their respective salts differ in certain physical properties such as solubility properties but they are otherwise equivalent for purposes of the invention.

The compounds of the invention can exist in solvated as well as unsolvated forms, including hydrated forms. In general, the solvated forms with pharmaceutically acceptable solvents such as water, ethanol and the like are equivalent to the unsolvated forms for purposes of the invention.

The compounds of the invention contain at least one center of assymetry, and the invention includes each isomer substantially separated from all other isomers as well as mixtures of isomers, including racemic mixtures.

The compounds of the invention are new chemical substances of value as pharmacological agents. More specifically they are analgesic agents useful for treating mammals suffering from pain. The following test procedures were utilized to establish the effectiveness of the compounds of formula I, and the indicated results were obtained.

Hot Plate Test—described in Woolfe, G., and McDonald, A. D., *The Evaluation of the Analgesic Action of Phethidine Hydrochloride (Demerol)*, J. Pharmacol. Exper. Therap. 80, 300 (1944); Eddy, N. B., Fuhrmeister-Touchberry, C., Liebermann, J. E., *Synthetic Analgesics I Methadon Isomers and Derivatives*, J. Pharmacol. Exper. Therap., 98, 121 (1950).

Pronounced analgesic action was observed in mice after the subcutaneous administration of 30–50 mg/kg. In addition to this action, a strong sedative action was ascertained after the administration of 50 mg/kg or more.

Phenyl-p-Quinone Test—described in Siegmund, E., Cadmus, R., and Lu, G., *A Method for Evaluating Both Non-Narcotic and Narcotic Analgesics*, Proc. Soc. Exper. Biol. Med., 95, 729 (1957).

In the Phenyl-p-Quinone test, the analgesic action in mice was weaker, than observed in the Hot Plate Test although still pronounced, after subcutaneous and intragastric administration.

The sedative effect observed in the Hot Plate Test was confirmed in mice by the Mobility Test [Turner, R. A., *Screening Methods in Pharmacology*, page 78, Academic Press, New York and London 1965].

The LD$_{50}$ values in mice, after intragastric administration of the compounds (as hydrochlorides) in water, were 400 mg/kg and above.

For the preparation of pharmaceutical compositions, at least one compound according to the present invention is mixed with a conventional liquid or solid pharmaceutical diluent or carrier. The compounds of the present invention can be administered orally or parenterally in liquid or solid form within a wide dose range.

Conventional additives for liquid compositions include, for example, tartrate and citrate buffers, ethanol and complexing agents (such as ethylene diaminetetraacetic acid and the non-toxic salts thereof), as well as high molecular weight polymers (such as liquid polyethylene oxide) for regulating the viscosity. Solid carriers include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycol). If desired, compositions suitable for oral administration can contain flavoring and sweetening agents.

Depending upon the severity of the symptoms being experienced, a single dose of a compound of the present invention will usually be within the range of 25–100 mg.

The invention is further illustrated by reference to the following examples.

EXAMPLE 1

(±)-1,2,3,4-Tetrahydro-7,10,11-trimethoxy-3-methyl-6-oxo-2,8a-methano-6H-dibenz(c,e)azocine 5.63 g. (15.74 mmol) 2-Methyl-6,7-dimethoxy-3-veratryl-1,2,3,4-tetrahydroisoquinoline (see Arch. Pharm., 297, 129/1964) is dissolved in 60 ml trifluoroacetic acid, while simultaneously cooling with ice-water and mixed dropwise, with the exclusion of moisture and under a protective nitrogen atmosphere and at a temperature of $-15°$ to $-10°$ C. with a solution of 4.20 g (2.5 equivalents) vanadyl trifluoride in 200 ml trifluoroacetic acid in the course of 5 minutes. After stirring for 1 hour at $-15°$ to $-10°$ C., the trifluoroacetic acid is distilled at ambient temperature and 100 mm Hg. The residue is mixed with water and extracted with chloroform. The combined chloroform extracts are washed with dilute aqueous ammonia solution. After drying and evaporation of the solvent the residue is crystallized from methanol/diethyl ether, yielding (±)-1,2,3,4-tetrahydro-7,10,11-trimethoxy-3-methyl-6-oxo-2,8a-methano-6H-dibenz(c,e)azocine, mp 168.5°–170° C., 4.55 g (85% of theory).

MS: M+ 341; IR (KBr): 1660, 1633, 1610 cm$^{-1}$

NMR (CDCl$_3$, δ): 2.54 (N—CH$_3$), 3.72, 3.77, 3.88 (3 x OCH$_3$), 5.94, 6.15, 6.77 (4 x 1H, s).

After treatment with methanolic aqueous hydrochloric acid and crystallization from methanol/diethyl ether, there is obtained the corresponding hydrochloride which decomposes at 250° C.

Analysis: C$_{20}$H$_{23}$NO$_4$.HCl calc.: C, 63.57%; H, 6.40%; Cl, 9.38%; N, 3.71%. found: C, 63.37%; H, 6.32%; Cl, 9.56%; N, 3.60%.

UV: λ$_{max}$ (MeOH) 242 nm (18400), 283 nm (5400).

EXAMPLE 2

(±)-1,2,3,4-Tetrahydro-7,10,11-trimethoxy-6-oxo-2,8a-methano-6H-dibenz(c,e)azocine 15.2 g (40 mmol) 6,7-Dimethoxy-3-veratryl-1,2,3,4-tetrahydroisoquinoline hydrochloride [see Ber., 73, 782 (1940)] is converted into the corresponding free base with aqueous ammonia. After extraction with chloroform and drying the extract, it is evaporated in vacuo and the residue is introduced at 0° C. into 110 ml trifluoroacetic acid. While stirring, a suspension of 12 g (100 mmol) vanadyl trifluoride in 370 ml trifluoroacetic acid is added dropwise to the solution within the course of 15 minutes at $-15°$ C. with the exclusion of moisture and under a protective atmosphere of nitrogen. The so obtained dark colored reaction mixture is stirred for another 45 minutes at $-10°$ C. and evaporated at 15°–20° C. at 100 mm Hg in the course of 1 hour. The residue is partitioned between water and chloroform. The chloroform phase is then treated with dilute aqueous ammonia. The organic phase is dried and evaporated in vacuo. The remaining yellowish foam crystallizes from methanol/diethyl ether in the form of colorless crystals. There is obtained (±)-1,2,3,4-tetrahydro-7,10,11-trimethoxy-6-oxo-2,8a-methano-6H-dibenz(c,e)azocine; mp 186°–187° C., 8.8 g (67% of theory).

MS: M+ 327

IR (KBr): 1655, 1633, 1610 cm$^{-1}$

NMR (CDCl$_3$, δ): 3.70, 3.73, 3.89 (3 x OCH$_3$), 5.93, 6.10, 6.50, 6.74 (4 x 1H, s).

Treatment of the base with methanolic hydrochloric acid gives the corresponding crystalline hydrochloride; mp 222°–226° C.

Analysis: C$_{19}$H$_{21}$NO$_4$.HCl calc.: C, 62.72%; H, 6.09%; Cl, 9.74%; N, 3.85%. found: C, 62.49%; H, 6.06%; Cl, 9.95%; N, 3.81%.

UV: λ$_{max}$ (MeOH) 238 nm (17200), 275 (6000)

EXAMPLE 3

(±)-1,2,3,4-Tetrahydro-7,10,11-triethoxy-3-methyl-6-oxo-2,8a-methano-6H-dibenz(c,e)azocine 8.9 g (21.5 mmol) 6,7-Diethoxy-3-(3,4-diethoxybenzyl)-2-methyl-1,2,3,4-tetrahydroisoquinoline (see Ber., 99, 2873/1966) is dissolved at 0° C. in 80 ml trifluoroacetic acid. While stirring, a solution of 6.6 g (2.5 equivalents) vanadyl trifluoride in 250 ml trifluoroacetic acid is added dropwise at $-15°$ C., with the exclusion of moisture and under a protective atmosphere of nitrogen. During the reaction, the reaction mixture becomes deep red-violet. The reaction mixture is stirred for another hour at $-10°$ C. and then worked up as described in Example 1. Crystallization from methanol gives (±)-1,2,3,4-tetrahydro-7,10,11-triethoxy-3-methyl-6-oxo-2,8a-methano-6H-dibenz(c,e)azocine; mp 158°–159° C., 5.9 g (72% of theory).

MS: M+ 383

IR (KBr): 1668, 1644, 1618 cm$^{-1}$

NMR (CDCl$_3$, δ): 1.4 and 4.0 (m, 3 x —O—CH$_2$—CH$_3$), 2.52 (N—CH$_3$), 5.89, 6.10, 6.50, 6.72 (4 x 1H, s).

Treatment of this product with methanolic hydrochloric acid and crystallization from methanol/diethyl ether gives the corresponding hydrochloride; mp 212°–215° C.

Analysis: C$_{23}$H$_{29}$NO$_4$.HCl calc.: C, 65.78%; H, 7.20%; Cl, 8.44%; N, 3.34%. found: C, 65.56%; H, 7.19%; Cl, 8.42%; N, 3.26%.

UV: λ$_{max}$ (MeOH) 238 nm (18100), 275 nm (5900).

EXAMPLE 4

(±)-1,2,3,4-Tetrahydro-7,11-dimethoxy-6-oxo-2,8a-methano-6H-dibenz(c,e)azocine 1.6 g (4.57 mmol) 3-(3-Methoxybenzyl)-6,7-dimethoxy-1,2,3,4-tetrahydroisoquinoline hydrochloride (mp 182°–186° C.) is converted to the free base with aqueous ammonia. Extraction with methylene chloride, drying and evaporation in vacuo gives the free base in the form of a yellowish oil. While cooling with ice water, the base is taken up in 10 ml trifluoroacetic acid. Within a period of 10 minutes, a suspension of 1.42 g (11.46 mmol) vanadyl trifluoride in 20 ml trifluoroacetic acid is added dropwise at a temperature of $-10°$ C.

After stirring for 1 hour at −10° C., the trifluoroacetic acid is evaporated at 20° C. in vacuo and the residue is partitioned between chloroform and water. The reaction mixture is worked up in known manner and 1.43 g of crude product in the form of the trifluoroacetate are obtained as a bright yellow syrup. Crystallization from methanol/acetone/diethyl ether gives (±)-1,2,3,4-tetrahydro-7,11-dimethoxy-6-oxo-2,8a-methano-6H-dibenz(c,e)azocine in the form of crystalline trifluoroacetate; mp 183°–187° C.

MS: M+ 297: base peak m/e 148
IR (KBr): 1656, 1638, 1632, 1608 cm$^{-1}$
NMR (DMSO, δ): 3.69, 3.74 (2 x —OCH$_3$), 6.20, 6.27 (2 x 1H), 6.93 (3H, m).

After treatment with aqueous ammonia and working up in the usual manner, the free base is obtained which, after recrystallization from methanol, melts at 182°–185° C.

UV: λ$_{max}$ (MeOH) 235 nm (20200), 277 nm (shoulder, 7700).

EXAMPLE 5

(±)-1,2,3,4-Tetrahydro-7-methoxy-10,11-methylenedioxy-6-oxo-2,8a-methano-6H-dibenz(c,e)azocine 5.3 g (14.6 mmol) (±)-3-(3,4-Methylenedioxybenzyl)-6,7-dimethoxy-1,2,3,4-tetrahydroisoquinoline hydrochloride is converted in known manner into the free base by treatment with ammonia and dissolved at a temperature 0° C. in 20 ml trifluoroacetic acid and mixed dropwise with the exclusion of moisture and under a nitrogen atmosphere at a temperature of −10° C. with a solution of 4.5 g (36.5 mmol) vanadyltrifluoride in 100 ml trifluoroacetic acid in the course of 10 minutes while stirring. The dark blue colored mixture is stirred for periods of one hour at temperatures of −10° C., 0° C., and 22° C. and the trifluoroacetic acid is distilled at ambient temperature and 100 Torr. The residue is mixed with water and extracted with chloroform. The unified chloroform extracts are washed with dilute aqueous ammonia. Drying, evaporation and crystallization from methanol gives (±)-1,2,3,4-tetrahydro-7-methoxy-10,11-methylenedioxy-6-oxo-2,8a-methano-6H-dibenz(c,e)azocine as a base; mp 199°–203° C.

MS: M+ 311
IR (KBr): 3010, 1658, 1640, 1610 cm$^{-1}$
NMR (DMSO-d$_6$; δ): 3,67 (OCH$_3$), 5.87 (3H, OCH$_2$O=CH—), 6.05 (1H, s), 6.45, 6.80 (2 x 1H, s)

Treatment of the free base with ethanolic hydrochloric acid and crystallization from ethanol/ether gives the hydrochloride of (±)-1,2,3,4-Tetrahydro-7-methoxy-10,11-methylenedioxy-6-oxo-2,8a-methano-6H-dibenz(c,e)azocine; mp 235°–238° C.

C$_{18}$H$_{17}$NO$_4$.HCl.0.5 H$_2$O: calc.: C, 60.58; H, 5.36; Cl, 9.94; N, 3.92. found: C, 60.95; H, 5.61; Cl, 9.75; N, 3.78.
UV: λ$_{max}$ (water) 241 nm (14 100), 288 nm (5400)

EXAMPLE 6

(±)-1,2,3,4-Tetrahydro-11-hydroxy-7-methoxy-6-oxo-2,8a-methano-6H-dibenz(c,e)azocine 0.9 g (3 mmol) (±)-3-(3-Hydroxybenzyl-6,7-dimethoxy-1,2,3,4-tetrahydroisoquinoline is dissolved at a temperature of 0° C. in a mixture of 10 ml absolute methylene chloride and 10 ml trifluoroacetic acid. Within a period of 5 minutes a solution of 0.34 ml (3.6 mmol) vanadyl chloride in 10 ml absolute methylene chloride are added dropwise to this solution in a protective gas atmosphere at a temperature of −10° C. The so obtained mixture is stirred for 1 hour at −10° C., whereupon, again, a solution of 0.17 ml vanadyl chloride in 5 ml absolute methylene chloride is added thereto. After stirring for 30 minutes at −10° C. and 90 minutes at 0° C. the mixture is concentrated at 20° C. in vacuo, the residue mixed with 20 ml water and extracted with chloroform/ether (8:2). The extract is worked up according to Example 1, which gives 0.74 g (±)-1,2,3,4-Tetrahydro-11-hydroxy-7-methoxy-6-oxo-2,8a-methano-6H-dibenz(c,e)azocine in the form of the crystalline trifluoroacetate. After treatment with aqueous ammonia solution the free base is obtained, which melts at a temperature of 265° C. (decomp.).

MS: M+ 283
IR (KBr): 3285, 1660, 1638, 1615 cm$^{-1}$
NMR (DMSO-d$_6$, δ): 3.67 (OCH$_3$), 5.95, 6.07 (2 x 1 H, s) 6.67 (3H, m)
Analysis: C$_{17}$H$_{17}$NO$_3$.¼H$_2$O: calc.: C, 71.17%; H, 6.01%; N, 4.76%. found: C, 70.93%; H, 6.13%; N, 4.86%.

EXAMPLE 7

(±)-3-Allyl-1,2,3,4-tetrahydro-7,10,11-trimethoxy-6-oxo-2,8a-methano-6H-dibenz(c,e)azocine 4 g (12.2 mmol) (±)-1,2,3,4-Tetrahydro-7,10,11-trimethoxy-6-oxo-2,8a-methano-6H-dibenz-[c,e]azocine is dissolved in 160 ml absolute ethanol and mixed with 1.72 g (14.2 mmol) allyl bromide. After addition of 2.5 g sodium hydrogen carbonate, the mixture is boiled for two hours under reflux in a nitrogen atmosphere. Subsequently, the solvent is extracted in vacuo. The product is obtained after partitioning the residue between aqueous ammonia solution and methylene chloride followed by work up of the organic phase in the known manner. There is obtained (±)-3-allyl-1,2,3,4-tetrahydro-7,10,11-trimethoxy-6-oxo-2,8a-methano-6H-dibenz(c,e)azocine; mp 203°–204° C., 3.8 g (77% of theory).

Analysis: C$_{22}$H$_{25}$NO$_4$.HCl: calc.: C, 65.42%; H, 6.49%; Cl, 8.78%; N, 3.47%. found: C, 65.51%; H, 6.40%; Cl, 8.75%; N, 3.41%.
IR(KBr): 1663, 1645, 1615 cm$^{-1}$
NMR (CDCl$_3$, δ): 3.73, 3.80, 3.87 (3 x OCH$_3$), 5.35–5.65 (3H, m), 5.96, 6.33, 6.48, 6.78 (4 x 1H, s)
UV: λ$_{max}$ (ethanol) 240 nm (16800), 280 nm (5200)

The starting material used is obtained according to Example 2.

EXAMPLE 8

(±)-3-[2-(3,4-Dimethoxyphenyl)ethyl]-1,2,3,4-tetrahydro-7,10,11-trimethoxy-6-oxo-2,8a-methano-6H-dibenz(c,e)azocine 2 g (6.1 mmol) (±)-1,2,3,4-Tetrahydro-7,10,11-trimethoxy-6-oxo-2,8a-methano-6H-dibenz[c,e]azocine and 1.65 g (6.7 mmol) 2-(3,4-dimethoxyphenyl)-ethylbromide are dissolved in 30 ml dimethylformamide and mixed with a granule of potassium iodide as well as with 3.5 g dry potassium carbonate. The mixture is heated under nitrogen for three hours at a temperature of 70° C. and for another three hours at 100° C. After cooling, the mixture is partitioned between water and methylene chloride. The crude product obtained after drying of the organic phase (sodium sulphate) and subsequent removal of the solvent is subjected to chromatographic purification on silica gel with chloroform as eluant. The base is then treated with hydrogen bromide and crystalized from methanol/acetic ester. There is obtained (±)-3-[2-(3,4-dimethoxyphenyl)ethyl]-1,2,3,4-tetrahydro-7,10,11-trimethoxy-6-oxo-2,8a-methano-6H- dibenz(c,e)azocine in the form of the colorless hydrobromide, which melts at a temperature of 206°–208° C.

Analysis: $C_{29}H_{23}NO_6 \cdot HBr$: calc.: C, 60,84%; H, 5.99%; Br, 13.96%; N, 2.45%. found: C, 60.87%; H, 5.82%; Br, 13.85%; N, 2.40%.

IR (KBR): 1662, 1645, 1615 cm$^{-1}$

NMR (CDCl$_3$, $\delta$): 3.75, 3.80, 3.86, 3.90, (15H, 5 x OCH$_3$), 5.97, 6.50, 6.37, (3 x 1H, s), 6.28 (3H, m), 7.00 (1H, s)

UV: $\lambda_{max}$ (Ethanol) 234 nm (25200). 279 nm (8600)

EXAMPLE 9

($\pm$)-3-Cyclopropylmethyl-1,2,3,4-tetrahydro-7,10,11-trimethoxy-6-oxo-2,8a-methano-6H-dibenz(c,e)azocine 4 g (12.2 mmol) ($\pm$)-1,2,3,4-Tetrahydro-7,10,11-trimethoxy-6-oxo-2,8a-methano-6H-dibenz[c.e.]azocine and 1.21 g (13.4 mmol) cyclopropylmethyl chloride are dissolved in 50 ml dimethyl formamide. After addition of 7 g dry potassium carbonate and a granule of potassium iodide the mixture is heated for three hours to 70° C., followed by heating for three hours to 100° C.

Working up as described in Example 8 and chromatographic purification on silica gel with chloroform/methanol (95:5) as an eluent gives the base in the form of a yellow syrup. Treatment with hydrogen bromide and crystallization from methanol/ether gives ($\pm$)-3-cyclopropylmethyl-1,2,3,4-tetrahydro-7,10,11-trimethoxy-6-oxo-1,8a-methano-6H-dibenz(c,e)azocine in the form of the yellowish hydrobromide; decomp.: 335° C.

MS (base): M$^+$ 381

Analysis: $C_{23}H_{27}NO_4 \cdot HBr$: calc.: C, 59.74%; H, 6.10%; Br, 17.28%; N, 3.03%. found: C, 59.56%; H, 6.11%; Br, 17.15%; N, 2.95%.

IR (KBr): 1670, 1650, 1620 cm$^{-1}$

NMR (DMSO-d$_6$, $\delta$): 0.4–0.8 (4H, m), 3.66, 3.73, 3.80 (3 x OCH$_3$), 6.17, 6.40, 6.55, 6.97 (4 x 1H, s)

EXAMPLE 10

($\pm$)-1,2,3,4-Tetrahydro-7,11-dimethoxy-3-(3-methyl-2-butenyl)-6-oxo-2,8a-methano-6H-dibenz(c,e)azocine 1 g (3.36 mmol) ($\pm$)-1,2,3,4-Tetrahydro-7,11-dimethoxy-6-oxo-2,8a-methano-6H-dibenz(c,e)azocine is dissolved in 15 ml absolute dimethyl formamide and mixed at ambient temperature with 0.35 g (3.36 mmol) 1-chloro-3-methyl-2-butene 1.6 g dry potassium carbonate, and 50 mg potassium iodide. While stirring, the mixture is heated for two and a half hours to 80° C. in a nitrogen atmosphere and subsequently evaporated at 40° C. in vacuo. The residue is partitioned between methylene chloride and water. The organic phase is worked up in known manner and yields a red-brownish oil, which is purified by chromatography on silica gel and/or crystallization from ethanol. There is obtained 0.8 g (65% of theory) ($\pm$)-1,2,3,4-tetrahydro-7,11-dimethoxy-3-(3-methyl-2-butenyl)-6-oxo-2,8a-methano-6H-dibenz(c,e)azocine in the form of colorless crystals having a melting point of 182°–184° C., 0.8 g (65% of theory).

MS: M$^+$ 365

Analysis: $C_{23}H_{27}NO_3$: calc.: C, 75.58%; H, 7.75%; N, 3.83%. found: C, 75.76%; H, 7.53%; N, 3.59%.

IR (KBr): 1655, 1635, 1610, 1600 cm$^{-1}$

NMR (CDCl$_3$, $\delta$): 1.69, 1.76, (2 x 3H, 2 x CH$_3$), 3.76, 3.79 (2 x OCH$_3$), 5.28 (1H, m) 5.90, 6.06 (2 x 1H, s) 6.53, 7.04 (3H, m)

The compound used as starting materials is obtained according to Example 4.

EXAMPLE 11

($\pm$)-3-Allyl-1,2,3,4-tetrahydro-7,11-dimethoxy-6-oxo-2,8a-methano-6H-dibenz(c,e)azocine 3.06 g (7.4 mmol) ($\pm$)-1,2,3,4-tetrahydro-7,11-dimethoxy-6-oxo-2,8a-methano-6H-dibenz(c,e)azocine hydrochloride is converted into the corresponding free base with aqueous ammonia solution. After extraction with methylene chloride, drying of the extract over sodium sulphate, filtration and removal of the solvent, the residue is dissolved in 100 ml absolute ethanol and mixed with 0.90 ml (10.4 mmol) allyl bromide, 1.8 g sodium hydrogen carbonate are added thereto. While stirring the mixture is heated to reflux in a nitrogen atmosphere for 90 minutes. The mixture is worked up as described in Example 7. After crystallization from ethanol/ether there is obtained ($\pm$)-3-allyl-1,2,3,4-tetrahydro-7,11-dimethoxy-6-oxo-2,8a-methano-6H-dibenz(c,e)azocine in the form of the colorless hydrochloride; mp 215° C.

Analysis: $C_{21}H_{23}NO_3 \cdot HCl$: calc.: C, 67.46%; H, 6.47%; Cl, 9.49%; N, 3.75%. found: C, 67.92%; H, 6.54%; Cl, 9.29%; N, 3.64%.

MS: (base) 337

IR (KBr): 1660, 1640, 1610, 1600 cm$^{-1}$

NMR (CDCl$_3$, $\delta$): 3.76 (2 x OCH$_3$), 5.00–5.40 (3H, m), 5.88, 6.03 (2 x 1H, s), 6.73 (3H, m)

UV: $\lambda_{max}$ 234 nm (20900), 275 nm (5600)

EXAMPLE 12

($\pm$)-3-[2-(3,4-dimethoxyphenyl)-ethyl]-1,2,3,4-tetrahydro-7,11-dimethoxy-6-oxo-2,8a-methano-6H-dibenz(c,e)azocine 2.02 g (6.05 mmol) ($\pm$)-1,2,3,4-Tetrahydro-7,11-dimethoxy-6-oxo-2,8a-methano-6-dibenz(c,e)azocine hydrochloride is dissolved in 35 ml absolute dimethyl formamide at ambient temperature and mixed with 1.63 g (6.66 mmol) 2-(3,4-dimethoxyphenyl)-ethylbromide, 3.50 g dry potassium carbonate and 0.25 g potassium iodide. While stirring, the mixture is heated for 20 hours at 80° C. in a nitrogen atmosphere, subsequently evaporated at 40° C. in vacuo and the residue partitioned between water and methylene chloride. After work up of the organic phase and chromatographic purification of the so obtained crude product on silica gel (Eluent: chloroform/methanol 98:2) there is obtained ($\pm$)-3-[2-,(3,4-dimethoxyphenyl)ethyl]-1,2,3,4-tetrahydro-7,11-dimethoxy-6-oxo-2,8a-methano-6H-dibenz(c,e)azocine as a base, which is converted into the hydrochloride in ethanol by addition of an equivalent amount of hydrogen chloride; mp 201°–203° C.

MS (base): M$^+$ 283

IR (KBr): 1675, 1655, 1625, 1615

Analysis: $C_{28}H_{31}NO_5 \cdot HCl \cdot 0.5 H_2O$ calc.: C 66.33%; H, 6.56%; Cl, 7.00%; N, 2.76%. found: C, 66.56%; H, 6.50%; Cl, 7.27%; N, 2.72%.

NMR (DMSO-d$_6$ $\delta$): 3.70, 3.77, (12H, 4 x OCH$_3$), 6.20, 6.31 (2 x 1H, s) 6.96 (6H, m)

We claim:

1. A compound having the structural formula:

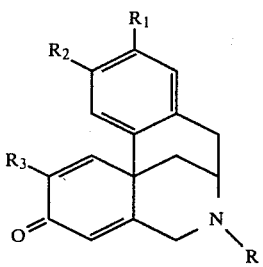

wherein R is hydrogen, branched or straight chain alkyl of from 1 to 3 carbon atoms, branched or straight chain alkenyl of 2 to 5 carbon atoms, cycloalkylalkyl of from 4 to 8 carbon atoms, or benzyl or phenethyl the aromatic rings of which may be optionally substituted by from 1 to 3 alkoxy groups of 1 to 3 carbon atoms or methylenedioxy; $R_1$ is hydroxy or alkoxy of from 1 to 3 carbon atoms; $R_2$ is hydrogen or alkoxy of from 1 to 3 carbon atoms; $R_1$ and $R_2$ when taken together may form a methylenedioxy group; $R_3$ is alkoxy of 1 to 3 carbon atoms; and the pharmacologically acceptable salts thereof.

2. A pharmaceutical composition for treating pain consisting essentially of an analgesic-effective amount of a compound as defined in claim 1 in combination with a pharmaceutically acceptable carrier.

3. A compound as defined in claim 1 wherein $R_1$ and $R_3$ may be the same or different and are methoxy or ethoxy, $R_2$ is hydrogen, methoxy or ethoxy, R is hydrogen, methyl, cyclopropylmethyl, branched or straight chain alkenyl of 2 to 5 carbon atoms, or 3,4-dimethoxyphenethyl, and the pharmacologically acceptable salts thereof.

4. The compound as defined in claim 1 which is (±)-1,2,3,4-tetrahydro-7,10,11-trimethoxy-3-methyl-6-oxo-2,8a-methano-6H-dibenz(c,e)azocine and the pharmacologically acceptable salts thereof.

5. The compound as defined in claim 1 which is (±)-1,2,3,4-tetrahydro-7,10-11-trimethoxy-6-oxo-2,8a-methano-6H-dibenz(c,e)azocine and the pharmacologically acceptable salts thereof.

6. The compound as defined in claim 1 which is (±)-1,2,3,4-tetrahydro-7,10,11-triethoxy-3-methyl-6-oxo-2,8a-methano-6H-dibenz(c,e)azocine and the pharmacologically acceptable salts thereof.

7. The compound as defined in claim 1 which is (±)-1,2,3,4-tetrahydro-7,11-dimethoxy-6-oxo-2,8a-methano-6H-dibenz(c,e)azocine and the pharmacologically acceptable salts thereof.

8. The compound as defined in claim 1 which is (±)-1,2,3,4-tetrahydro-7-methoxy-10,11-methylenedioxy-6-oxo-2,8a-methano-6H-dibenz(c,e)azocine and the pharmacologically acceptable salts thereof.

9. The compound as defined in claim 1 which is (±)-1,2,3,4-Tetrahydro-11-hydroxy-7-methoxy-6-oxo-2,8a-methano-6H-dibenz(c,e)azocine and the pharmacologically acceptable salts thereof.

10. The compound as defined in claim 1 which is (±)-3-allyl-1,2,3,4-tetra-hydro-7,10,11-trimethoxy-6-oxo-2,8a-methano-6H-dibenz(c,e)azocine and the pharmacologically acceptable salts thereof.

11. The compound as defined in claim 1 which is (±)-3-[2-(3,4-dimethoxyphenyl)ethyl]-1,2,3,4-tetrahydro-7,10,11-trimethoxy-6-oxo-2,8a-methano-6H-dibenz(c,e)azocine and the pharmacologically acceptable salts thereof.

12. The compound as defined in claim 1 which is (±)-3-cyclo-propylmethyl-1,2,3,4-tetrahydro-7,10,11-trimethoxy-6-oxo-1,8a-methano-6H-dibenz(c,e)azocine and the pharmacologically acceptable salts thereof.

13. The compound as defined in claim 1 which is (±)-1,2,3,4-tetrahydro-7,11-dimethoxy-3-(3-methyl-2-butenyl)-6-oxo-2,8a-methano-6H-dibenz(c,e)azocine and the pharmacologically acceptable salts thereof.

14. The compound as defined in claim 1 which is (±)-3-allyl-1,2,3,4-tetrahydro-7,11-dimethoxy-6-oxo-2,8a-methano-6H-dibenz(c,e)azocine and the pharmacologically acceptable salts thereof.

15. The compound as defined in claim 1 which is (±)-3-[2-(3,4-dimethoxyphenyl)ethyl]-1,2,3,4-tetrahydro-7,11-dimethoxy-6-oxo-2,8a-methano-6H-dibenz(c,e)azocine and the pharmacologically acceptable salts thereof.

16. A process for preparing a compound as defined in claim 1 which comprises treating a compound having the structural formula II

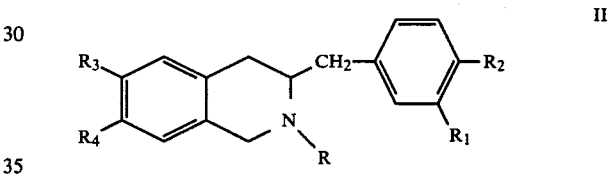

with an oxidizing agent in the presence of a strong acid at a temperature of from −15° C. to +30° C.; wherein R, $R_1$, $R_2$ and $R_3$ are as defined in claim 2 and $R_4$ is hydroxy, alkoxy of from 1 to 6 carbon atoms or benzyloxy.

17. The process as defined in claim 16 wherein the oxidizing agent is vanadyl trifluoride.

18. The process as defined in claim 16 wherein the oxidizing agent is vanadyl trichloride.

19. The process as defined in claim 16 wherein R is hydrogen.

20. The process as defined in claim 19 wherein the product is N-substituted with a group R' wherein $R^1$ is branched or straight chain alkyl of from 1 to 3 carbons, branched or straight chain alkenyl of 2 to 5 carbon atoms, cycloalkylalkyl of from 4 to 8 carbon atoms, or benzyl or phenethyl the aromatic rings of which may be optionally substituted by from 1 to 3 alkoxy groups of 1 to 3 carbon atoms or methylenedioxy.

21. The process as defined in claim 20 wherein the N-substitution is accomplished using a compound R'—X wherein X is chlorine, bromine or iodine.

22. A method for relieving pain in a mammal which comprises administering to a mammal in need thereof the composition as defined in claim 2.

* * * * *